United States Patent [19]

Miziolek

[11] Patent Number: 4,620,095
[45] Date of Patent: Oct. 28, 1986

[54] ION NEUTRALIZATION RESONANCE EMISSION ELEMENTAL DETECTOR

[76] Inventor: Andrzej W. Miziolek, 200 Cable St., Caltimore, Md. 21210

[21] Appl. No.: 571,894

[22] Filed: Jan. 18, 1984

[51] Int. Cl.$^4$ .............................................. H01J 49/00
[52] U.S. Cl. ...................................... 250/281; 250/285
[58] Field of Search ............... 250/251, 281, 285, 289, 250/282, 283, 423 D, 306, 307, 309; 376/107, 127, 128, 129

[56] References Cited

U.S. PATENT DOCUMENTS

| 3,619,605 | 11/1971 | Cook et al. | 250/283 |
| 3,767,925 | 10/1973 | Foley, Jr. et al. | 250/251 |
| 3,846,636 | 11/1974 | Zehr et al. | 250/251 |
| 3,890,535 | 6/1975 | Gautherin et al. | 250/423 R |
| 4,469,942 | 9/1984 | Srivastara | 250/252.1 |

FOREIGN PATENT DOCUMENTS 0056299  5/1977  Japan .................................. 250/251

OTHER PUBLICATIONS

Osherovich et al, An Installation with Crossed Beams for Measurement of the Radiation Lifetimes of the Excited States of Atoms, Ions, and Molecules, Inst. and Exp. Tech., vol. 18, Nov.-Dec. 1975.
Scott et al, The Electron Beam Fluorescence Method as Applied to Molecular Scattering Experiments, Rev. Sci. Lust., vol. 45, Feb. 1974.

Primary Examiner—Bruce C. Anderson
Assistant Examiner—Paul A. Guss
Attorney, Agent, or Firm—Anthony T. Lane; Robert P. Gibson; Michael C. Sachs

[57] ABSTRACT

A device and method is disclosed for detecting elemental ions by colliding a beam of the elemental ions with a beam of collision partners having an opposite charge to generate element specific radiation. The radiation whose wavelength is specific to the element is filtered and detected as a measure of the elemental ion. In one case using energy matched collision exchange partners, metal ions of an opposite charge are used as collision partners.

14 Claims, 4 Drawing Figures

ION NEUTRALIZATION RESONANCE EMISSION ELEMENTAL DETECTOR

The invention described herein may be manufactured, used and licensed by or for the Government for Governmental purposes without the payment to me of any royalties thereon.

FIELD AND BACKGROUND OF THE INVENTION

The present invention relates in general to detectors for detecting trace elements and, in particular, to a new and useful ion neutralization resonance emission elemental detector which can be used with or without a mass spectrometer or suitable substitute to detect very low levels of elemental ions.

Trace elemental detection is currently accomplished by numerous techniques. Some major ones include atomic absorption spectroscopy (AAS), atomic fluorescence spectroscopy (AFS), inductively coupled plasma atomic emission spectroscopy (ICP-AES), arc/spark/laser emission spectroscopy (AES), laser ablation mass spectrometry (LAMMA), neutron activation analysis (NAA) and X-ray fluorescence (XRF). Although generally quite different from one another, these instruments share at least two major characteristics; they usually are rather bulky in size and have high capital equipment costs associated with them.

The majority of these instruments exploit the inherently sensitive and elemental specific process of absorption or emission of radiation due to electronic transitions. This analytically very attractive feature is utilized in the present invention as well.

SUMMARY OF THE INVENTION

The present invention is a relatively simple, low cost and compact device for the sensitive and specific detection of trace quantities of various elements. It is primarily meant to be used as a detector for mass spectrometers. In specific instances, however, this device can be directly coupled to an ionization source so that a mass spectrometer is not necessary.

Accordingly an object of the invention is to provide a detector for detecting an analyte ion having one charge and supplied in a first beam comprising, a housing defining a detector chamber, vacuum means for establishing a partial vacuum in the detector chamber, collision partner source means connected to the housing for supplying a second beam of collision partner ions having an opposite charge into the chamber in a direction to intersect and collide with the first beam to produce resonant radiation, filter means connected to the housing for filtering all but the resonant radiation and a photodetector connected to the filter means for detecting the resonant radiation which corresponds to the amount of analyte ion present in the first beam.

Another object of the invention is to provide a method of detecting an analyte ion having one charge and supplied in a first beam by intersecting the first beam with a second beam of collision partner ions of opposite charge and detecting the emitted resonant radiation.

The invention has various advantages over existing systems.

As a detector in a mass spectrometer, the trace element analysis is done by detection of wavelength specific photons from the analyte element rather than the traditional mass spectrometric charge or current detection. This gives an added degree of selectivity and thus greatly improves discrimination against noise ions of similar m/e (mass to electrical charge ratio for the ions). This is particularly important when using lower resolution mass spectrometers.

By using the mass spectrometer (or a suitable substitute) to give time and space separation from the original ionization in the source region, the background luminescence during photon detection is significantly decreased. This is in sharp contrast to the traditional trace element detection techniques mentioned above where the element specific emission is generated in a high temperature (luminous) environment where background photon interference emissions frequently define the noise level and therefore the limit of detection of an analysis.

The analyte ions, with or without a mass spectrometer, can be manipulated for subsequent analysis by suitable electric and magnetic fields. Traditional trace element detectors deal with neutral absorbing or emitting analyte atoms which cannot be readily manipulated.

With negligible background luminescence in the detector region, inherently sensitive detectors, such as photon counters, can be utilized.

The working principle at the detector is inherently simple. The invention should be low cost, easily manufactured and relatively compact. It does not require any particularly sophisticated or state-of-the-art components.

Instruments like the laser ablation mass spectrometer (LAMMA) should benefit greatly due to the discrimination against noise ions mentioned above. With a calculated absolute detection limit in the $10^{-16}$ gram range, sub parts-per-million (ppm) sensitivity (assuming $10^{-6}$ gram of material ablated) is indicated.

The inherent sensitivity translates into low sample size requirements.

The use of Energy Matched Collision Exchange Partner (EMCEP) concept may eliminate the need for a mass spectrometer altogether thus greatly simplifying construction and operation as well as lowering capital equipment costs substantially.

Accordingly another object of the invention is to provide a new, high performance trace element detector which is useful alone or results in an improvement of the "effective" mass resolution of low resoution (inexpensive) mass spectrometers, and is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
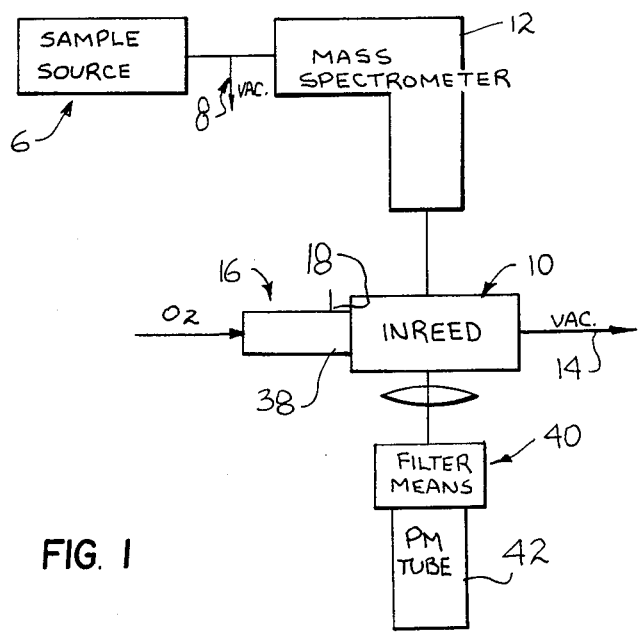
FIG. 1 is a block diagram showing the inventive detector, referred to as an ion neutralization resonance emission elemental detector or INREED for short.

Referring to the drawings in particular, the invention therein, as shown in FIG. 1, comprises a detector for sensing analyte element specific emission in the form of wavelength specific radiation which is produced as a result of a collision between an elemental (analyte) ion and a collision partner. The detector generally designated 10 can advantageously be connected to a mass spectrometer 12. Any other source of ions may be utilized such as an ion storage device or an ion drift region. The ion storage device may be in the form of ion cyclotron resonance (ICR). The mass spectrometer may be of the magnetic sector type, the quadrupole type or the time-of-flight type. Since mass spectrometers are well known in the art, details thereof will not be provided here.

A mass spectrometer is connected to a sample ionization region 6 and includes a vacuum pump 8 in known fashion.

The INREED detector 10 receives an ion beam from mass spectrometer 12. A second beam containing collision partners is generated by collision partner source means generally designated 16, to be described in greater detail hereinunder. Valve 18, shown here only symbolically, controls the inflow of oxygen shown here into element 16. Another vacuum pump 14 is provided for the chamber of the detector. Alternately, the same pump 8 utilized to evacuate the mass spectrometer may be connected to the detector as well.

An effusive beam light baffle 38 is provided as a part of the collision partner source means 16 for shielding the interior of detector 10 from background light.

Filter means generally designated 40 are provided for focusing and filtering the resonant radiation so that only radiation due to the collision is provided to a photodetector 42 which is of any sensitive type and preferably a photomultiplier tube.

I have discovered the key element of the invention which can be summarized by the reaction:

$$A^+ + X \rightarrow A^* + X' = A + h\nu + X' \qquad (1)$$

where $A^+$ = analyte ion, $X$ = colliding partner, $A^*$ = electronically excited neutral analyte element A and $h\nu$ = analyte element specific radiation and $X'$ is the neutralized colliding partner or positively charged, in the case of a neutral atomic beam collision partner source. Reaction (1) will be thermochemically driven because the collision partner (X) will always be chosen so that the (change in) electron affinity by equation (2), $\Delta H_r° \leq 0$. Simply stated, the invention is based upon the fact that wavelength specific radiation will be emitted by the analyte element as a consequence of the neutralization/stabilization of the initial analyte ion $(A^+)$.

In the role of a mass spectrometer detector the inventive device can utilize a number of possibilities for the collision partner (X). These include, but are not necessarily limited to, a beam of electrons, $O_2^-$, a collision partner (such as many metallic atoms) whose ionization potential (I.P.) is less than that for the analyte element (A) or an appropriate colliding surface.

As an example, the case of $X = O_2^-$ will be considered. The electron affinity (EA) of $O_2$, a property of the Oxygen, is demonstrated in the relations:

$$O_2 + e^- > O_2^-; \Delta H_r° > EA = -0.5 \text{ electron volts (e.v.)} \qquad (2)$$

If we substitute $O_2^-$ for X in reaction (1), then $X' = O_2$ and the $\Delta H_r° = -(I.P.)_A - (-0.5 \text{ e.v.})$. This means that as a result of reaction (1), $A^*$ will be in a highly excited electronic state which is approximately 0.5 e.v. below the ionization potential energy. This is a very probable occurrence since the density of states for most elements is quite high near their ionization limit and thus the amount of translational energy that needs to be taken up or deposited in the reaction (called the Energy Defect) is quite low.

Having produced $A^*$ in an excited electronic state, energy equilibration with the ground electronic state surrounding needs to occur. To do this there are a number of channels available for energy release including inelastic collisions and the emission of radiation. The emission channels are enhanced for atoms since their rates are comparatively fast for strong transitions (averaging $10^8$ to $10^9$ photons per second). Furthermore, these strong transitions involve line emissions which makes their detection very specific by good wavelength discrimination against background interference emission. This situation for analyte element ions can be sharply contrasted to the case involving neutralization and deactivation of molecular ions. Here, the vibrational and rotational degrees of freedom will assume important roles in terms of energy release pathways. From a practical standpoint, they will dilute any emission that occurs due to the nature of molecular band emission. Furthermore, the rates for emission will generally be slower than those for atoms (averaging $10^5$ to $10^8$ photons per second) and collisions which may promote emission signal depleting curve crossing into dissociative of long lived metastable states may be important. Thus, a strong argument is made that in the role of a mass spectrometer detector the invention will be able to discriminate very well against interference ions of similar m/e value and in favor of analyte ion detection.

The inventive device can be utilized as a detector for a mass spectrometer with $O_2^-$ as the neutralization/deactivation gas. The exit slits of a known mass spectrometer pass the analyte ions $(A^+)$ and all the other interfering ions of similar m/e, through into a detector region of the device. The trace element analyte ions $(A^+)$ will be in their ground electronic state along with the interference ions so that the background luminescence should be zero or very low.

Inside the detector region the ion beam from the mass spectrometer will cross and collide with the $O_2^-$/buffer gas effusive beam. The neutralization/deactivation collisions will occur and the element characteristic wavelength specific light emission will result. This emission is collected by a fast lens and focused onto a wavelength dispersion device (e.g. monochromator) or even just an analytical filter. Then the photons are detected by a sensitive photodetector (e.g. photomultiplier, diode array, etc.). The lack of strong background luminescence enables photon counting to be employed.

Figure 4:
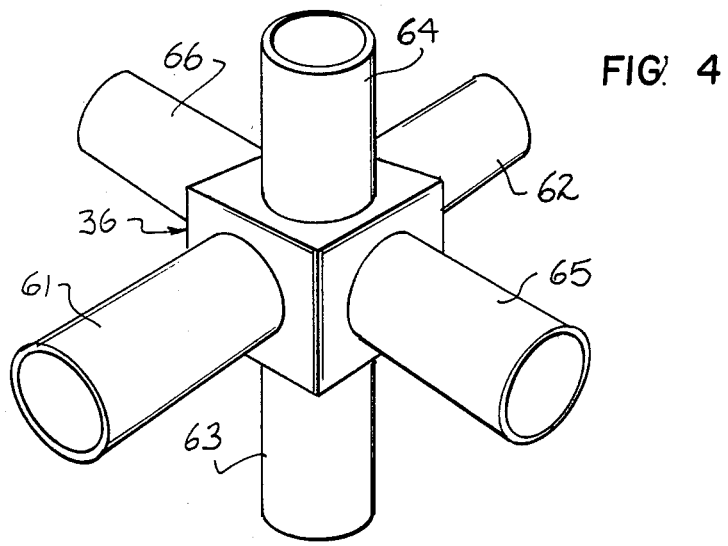
FIG. 4 is a perspective view of a six-cross housing which can advantageously be utilized to define the detector chamber of the invention.
Figure 2:
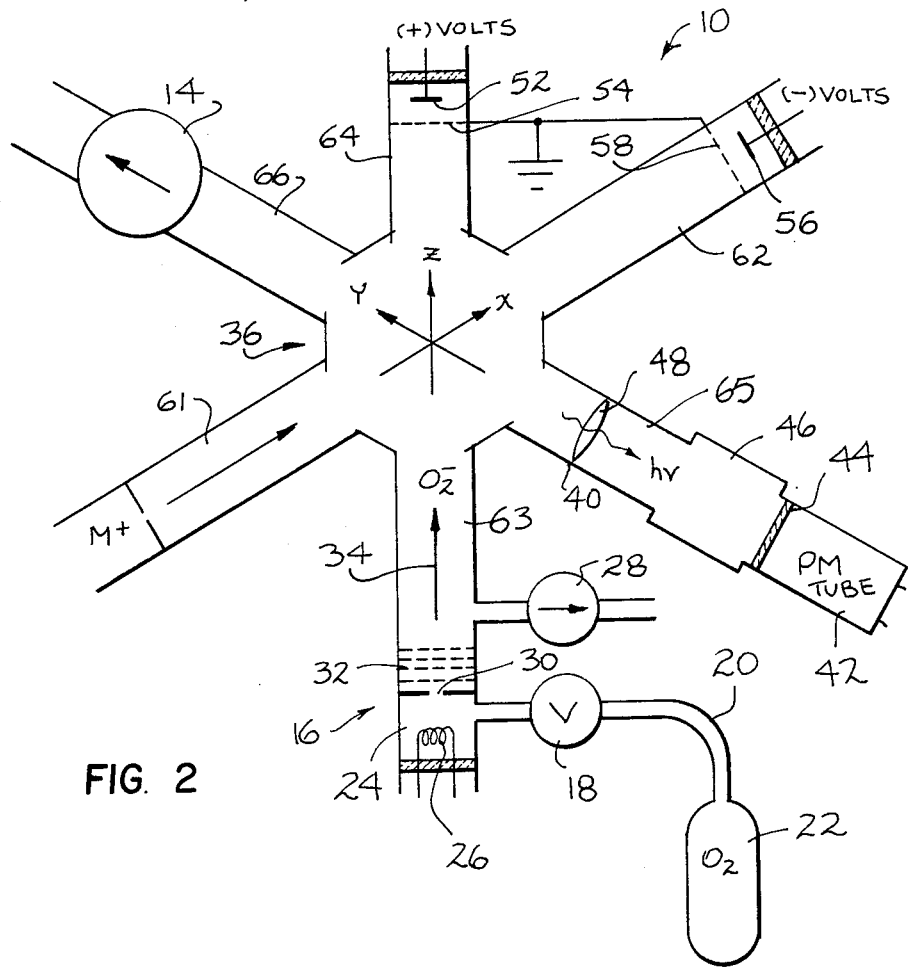
FIG. 2 is a schematic representation of the INREED in accordance with the invention.

Referring to FIG. 2, a six cross housing 36 is shown which defines a chamber. As shown in FIG. 4, a six way cross manufactured by Huntington Labs and identified as model VF-6001 can be utilized to define a detector chamber. Housing 36 includes six ports number 61 through 66. Ports 61, 62 are axially aligned with each other and lie on axis identified as X in the housing chamber. Ports 65,66 are similarly aligned on axis Y and disposed at 90° to ports 61, 62. Similarly, ports 63, 64 lie on axis Z which is mutually offset by 90° from axes X and Y.

The source of ion in the form of the first ion beam identified as M+ is supplied through a slit and port 61 to the detector chamber. The collision partner source 16 includes a source of oxygen in the form of bottle 22 and oxygen line 20. Oxygen is supplied under pressure over valve 18 into a tungsten filament chamber 24 which contains a tungsten heating filament 26. The oxygen gas is heated and ionized into $O_2^-$ collision partners. The oxygen flow may be buffered with a buffer gas or pure oxygen. The pressure in chamber 24 is maintained in the millitorr region to promote high conversion of oxygen to oxygen ion. Vacuum pump 28 maintains this low pressure.

The second beam of oxygen ion collision partners is then formed by a slit 30 in a plate above the tungsten filament 26 which is biased at about 5 to 10 volts with respect to the source potential. The beam is focused by electrical focusing lenses 32 into the second beam 34 which is directed through port 63 into the detector chamber to collide with the first beam.

The collector chamber is previously evacuated to the micrometer of Hg pressure range using the vacuum pump 14 or, as noted above, the vacuum pump which is necessary for the mass spectrometer. The vacuum pump 14 may for example be a Cole-Parmer model C-7066-10.

The analyte element specific radiation which is emitted by this collision is conducted along port 65 through a lens 48 which forms a part of the filter means 40. Filter means 40 may include a simple analytical filter 44 where the light is sufficiently strong in the element specific emission line with a high signal-to-noise ratio. Alternately, that is instead of filter 44, a monochromator for passing all but the wavelength of interest, designated 46 is utilized. Alternately, both the monochromator and filter 44 can be used as shown in FIG. 2.

Beyond these filter means is a photodetector which is preferably a photomultiplier tube 42 of known design. This may for example be the EMI Model QL-30 photo tube housing with EMI 9529 photocounter tube therein. The monochromator may be Oriel Model 7240 and the filter may be the Oriel analytical line 5700 series.

The special case of the Energy Matched Collision Exchange Partner (EMCEP) will now be discussed. By choosing an appropriate collision partner, a metal atom, whose I.P. is lower than that of A, a special condition can be engineered such that the $\Delta H_r°$ for reaction (1) matches very closely to a particular excited state of A which in turn is strongly radiatively coupled with a lower state. In this situation the rate of reaction (1) will be maximized into this particular state since the Energy Defect is minimized and the particular emission wavelength to monitor becomes fixed. In practice, this approach will be particularly useful for certain elements (given in the Table) whose I.P.'s are in the 5 to 11 e.v. region. In this case the mechanical arrangement will be similar to that given in FIG. 1 except that the $O_2/W$ filament will be replaced by the appropriate metal atom effusive flow furnace that is optically well baffled.

TABLE

| A<br>Element<br>(I.P.) | B<br>Allowed Level/<br>Transition (Å) | C<br>(A-B) | D<br>Possible<br>Collision<br>Partner (I.P.) | E<br>Energy<br>Defect<br>(C-D) |
|---|---|---|---|---|
| Hg<br>(10.44 e.v.) | 4.89 e.v./2537Å | 5.55<br>e.v. | Sr (5.69 e.v.) | −0.14<br>e.v. |
| Cd (8.99) | 3.80/3261 | 5.19 | Ba (5.21) | −0.02 |
| Ag (7.57) | 3.78/3280 | 3.79 | Cs (3.89) | −0.10 |
| Au (9.22) | 5.10/2427 | 4.12 | Rb (4.18) | −0.06 |
| Se (9.75) | 5.97/2074 | 3.78 | Cs (3.89) | −0.11 |
| Ti (6.82) | 2.47/5014 | 4.35 | K (4.34) | 0.01 |
| V (6.74) | 2.86/4330 | 3.88 | Cs (3.89) | −0.01 |
| Zn (9.39) | 4.03/3076 | 5.36 | Li (5.39) | −0.03 |
| Cu (7.72) | 3.82/3247 | 3.90 | Cs (3.89) | 0.01 |
| Ni (7.63) | 3.68/3369 | 3.95 | Cs (3.89) | 0.06 |
| Co (7.86) | 3.57/3474 | 4.29 | K (4.34) | −0.05 |
| P (10.97) | 7.17/2149 | 3.80 | Cs (3.89) | −0.09 |

Figure 3:
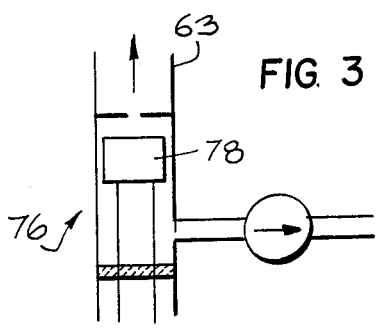
FIG. 3 is a schematic representation of an alternate collision partner source which utilizes metal atoms.

Turning to FIG. 3, the alternate collision partner source 76 is shown utilizing a stainless steel resistivity heated oven 78 which replaces the tunsten filament 26.

Here, the particular candidate collision metal of choice is placed inside and heated so that an effusive atomic means emerges with a flow rate similar to that of $O_2^-$. In this case, any metal atoms that undergo a charge transfer collision with the first M+ beam and other ions, will be trapped by ion collector plates 52 and 56 attached to ports 64 and 62 shown in FIG. 2 which are biased with a respective positive and negative voltage to collect stray respective negative and positive ions.

As shown in FIG. 2, port 64 contains a positive voltage supply plate 52 and a screen 54 which attracts excess oxygen ions. Port 62 includes a negative voltage supply plate 56 and a screen 58. Plate 56 attracts excess mass spectrometer ions or M+ ions. Screens 54 and 58 are connected together and grounded.

The central element of this invention is the use of analyte element specific light emission for the purpose of detecting trace quantities of various elements which are provided in a non-radiating ionic form.

To get an approximate idea of the utility of this invention with respect to detection limits of trace element, a simple calculation can be performed with appropriate assumptions. First assume that the photometric efficiency (geometric collection efficiency, quantum yield, monochromator throughput, etc.) is on the order of $10^{-4}$; photometric efficiency being a measure of the proportion of light which gets through to collection. With appropriate design and use of light baffles background radiation should be negligible. Also, an experimentally determined optimum collision gas effective pressure (probably in the mtorr to torr range) should be found so that each ion entering from the exit slits of the mass spectrometer undergoes a neutralization collision as in reaction (1). Then, with a photon counting tube whose dark count is 1/sec, for a signal-to-noise ratio (SNR)=1, one gets $10^6$ ions of the analyte element (A+)/sec as the detection limit. This corresponds to a current of approximately $10^{-13}$ amps or, assuming an average atomic weight of 100 grams/mole, to approximately $10^{-16}$ grams/sec. For an integration time of 1 sec, the absolute detection limit is $10^{-16}$ grams. This can be compared to experimentally determined detection limits for the other trace element analytical techniques mentioned before, which range from $10^{-9}$ to $10^{-15}$ grams. The comparison is therefore quite favorable.

While specific embodiments of the invention has been shown and described in detail to illustrate the application of the principles of the invention, it will be understood that the invention may be embodied otherwise during departing from such principles.

What is claimed is:

1. Machine for selectively detecting presence of particular analyte trace elements in a given positively ionized beam of particles, including distinguishing a particular analyte from other elements having the same m/e, mass to charge ratio, comprising:

means for forming a negatively ionized oxygen beam for collision with said given particle beam;

evacuated chamber means in which the said positively and negatively ionized beams are collided;

means for viewing light coming from the intersection of said beams' collision at select frequencies of analysis;

whereby light photons emanating from said collision at select viewed frequencies, indicative of resonant behavior unique to particular known element, identifies the particular analyte element under analysis.

2. Apparatus for selectively detecting pressure of particular analyte trace elements in a given ionized beam of particles, including distinguishing a particular analyte from other elements having the same m/e, mass to charge ratio, comprising:

means for forming an ionized particle beam of a preselected collision element unique for the particular analyte sought under analysis, of opposite charge to the said given particle beam, for collision therewith;

evacuated chamber means in which the said positively and negatively ionized beams are collided;

means for viewing light coming from the intersection of said beams' collision at select frequencies of analysis;

whereby light photons emitting from said collision at select viewed frequencies, indicative of resonant behavior unique to a particular known element, identifies the particular analyte element under analysis.

3. Apparatus for selectively detecting presence of particular analyte trace elements in a given ionized beam of particles, including distinguishing a particular analyte from other elements having the same m/e, mass to charge ratio, comprising:

means for forming a beam of a select collision element, of the opposite charge to the said given particle beam for collision therewith;

evacuated chamber means in which the said oppositely charged ionized beams are collided;

means for viewing light coming from the intersection of said beams' collision at select frequencies of analysis;

whereby light photons emanating from said collision at select viewed frequencies, indicative of resonant behavior unique to a particular known element, identifies the particular analyte element under analysis.

4. Apparatus for selectively detecting presence of particular analyte trace elements in a given ionized beam of particles, comprising:

means for forming an ionized beam of a select collision element of the opposite charge to the said given particle beam for collision therewith;

evacuated chamber means in which the said oppositely charged ionized beams are collided forming a neutral particle with combined photoemission of light;

means for viewing light coming from the intersection of said beams' collision at select frequencies of analysis;

whereby light photons emanating from said collision at select viewed frequencies, indicative of resonant behavior unique to a particular known element, identifies the particular analyte element under analysis.

5. Apparatus as in claim 2 wherein the source of the said given ionized beam of particles, is an exit beam from a mass spectrometer.

6. Apparatus as in claim 2 wherein the source of the said given ionized beam of particles, is formed by striking a given material which includes the analyte element under analysis, with a laser.

7. Apparatus as in claim 2 wherein the collision elements could comprise electrons, when a negatively charged collision beam is required, and comprise protons, when a positively charged collision beam is required.

8. Apparatus as in claim 2, wherein the source of said collision element beam comprises a source of ionizible elemental gas, a heating chamber connected to said housing and to said source of gas for ionizing the gas and electrical focusing means connected between said housing and said heating chamber for focusing the ionized elemental gas into said collision beam.

9. Apparatus as in claim 2, wherein the source of said collision element beam comprises an oven for generating metal vapor and focusing means for focusing said metal vapor into said collision beam.

10. Apparatus as in claim 2 wherein said means for viewing light comprises a filter means including a monochromator, and a photodetector comprising a photomultiplier tube.

11. Apparatus as in claim 2, wherein said means for viewing light comprises a filter means including an analytical light filter and a photodetector comprising a photomultiplier tube.

12. Apparatus as in claim 2, wherein said evacuated chamber means comprises a housing which includes six ports connected to a central chamber, a first one of said ports adapted for receiving the given beam, a second of said ports connected to receive said collision element beam, a third one of said ports connected to said means for viewing light, for conducting the resonant radiation therealong, a fourth of said ports connected to a vacuum means for establishing a partial vacuum in said chamber, and an electrically chargeable plate in each of the fifth and sixth of said chambers, one of said plates adapted to be charged to a polarity for attracting excess analyte ions and the other of said plates adapted to be charged to a polarity for attracting excess collision ions.

13. Apparatus as in claim 12, including a grid screen in each of said fifth and sixth ports between said chamber and each of said plates, respectively, said grid screens being electrically conducted to each other and grounded.

14. Apparatus as in claim 13, wherein said housing with ports comprises a six-way cross chamber with three mutually perpendicular axes, said first and fifth ports lying coaxially on a first one of said axes, said second and sixth ports lying coaxially on a second of said axes and said third and fourth ports lying coaxially on a third of said axes.

* * * * *